United States Patent
Kubo (10) Patent No.: US 8,911,241 B2
(45) Date of Patent: Dec. 16, 2014

(54) SUBSTRATE CONNECTION STRUCTURE

(71) Applicant: Olympus Medical Systems Corp., Tokyo (JP)

(72) Inventor: Takafumi Kubo, Akiruno (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/165,723

(22) Filed: Jan. 28, 2014

(65) Prior Publication Data

US 2014/0187060 A1    Jul. 3, 2014

Related U.S. Application Data (63) Continuation of application No. PCT/JP2013/078164, filed on Oct. 17, 2013.

(30) Foreign Application Priority Data

Nov. 29, 2012  (JP) .................................. 2012-261196

(51) Int. Cl.
| | |
|---|---|
| H01R 12/00 | (2006.01) |
| H01R 13/58 | (2006.01) |
| H05K 3/36 | (2006.01) |
| G02B 23/24 | (2006.01) |
| A61B 1/04 | (2006.01) |
| H05K 1/14 | (2006.01) |
| H01R 12/71 | (2011.01) |

(52) U.S. Cl.
CPC .................. *H01R 13/58* (2013.01); *H05K 3/36* (2013.01); *G02B 23/24* (2013.01); *A61B 1/04* (2013.01); *H05K 1/14* (2013.01); *H01R 12/716* (2013.01)
USPC ............................................. 439/65; 49/352

(58) Field of Classification Search
CPC ........ H01R 13/58; H01R 12/716; H05K 1/14; H05K 3/36; G02B 23/24; A61B 1/04
USPC .............................. 439/65–73, 352, 367–370
See application file for complete search history.

(56) References Cited

U.S. PATENT DOCUMENTS

| | | | | |
|---|---|---|---|---|
| 3,550,062 | A | * 12/1970 | Drenten et al. ................. | 439/64 |
| 5,569,158 | A | 10/1996 | Suzuki et al. | |
| 8,292,630 | B1 | * 10/2012 | Bobuk ............................ | 439/65 |
| 8,500,456 | B1 | * 8/2013 | Holec et al. .................... | 439/65 |
| 2007/0164444 | A1 | 7/2007 | Sekido et al. | |
| 2009/0292169 | A1 | 11/2009 | Mitani et al. | |

FOREIGN PATENT DOCUMENTS

| | | |
|---|---|---|
| EP | 2 134 209 A1 | 11/2009 |
| JP | 07-111979 A | 5/1995 |

(Continued)

*Primary Examiner* — Khiem Nguyen
(74) *Attorney, Agent, or Firm* — Scully, Scott, Murphy & Presser, P.C.

(57) ABSTRACT

A substrate connection structure includes: a first substrate having stiffness with a first connector mounted on a front face; a second substrate having stiffness with a second connector detachably attached to the first connector mounted on a front face facing the front face of the first substrate; and a restricting member including a projection portion, the restricting member including a plate-like member and being detachably attachable to the first substrate by being moved along a planar surface of the first substrate, the projection portion projecting from the front face of the first substrate and regulating a position of the second substrate relative to the first substrate in a state in which the restricting member is attached to the first substrate, and limiting a direction in which the second substrate is detached when the second connector mounted on the second substrate is detached from the first connector on the first substrate.

11 Claims, 6 Drawing Sheets

(56) References Cited

FOREIGN PATENT DOCUMENTS

| | | |
|---|---|---|
| JP | 2005-129866 A | 5/2005 |
| JP | 2007-173583 A | 7/2007 |
| JP | 2007-234736 A | 9/2007 |
| JP | 2009-277534 A | 11/2009 |
| JP | 2009-279148 A | 12/2009 |

* cited by examiner

SUBSTRATE CONNECTION STRUCTURE

CROSS REFERENCE TO RELATED APPLICATION

This application is a continuation application of PCT/JP2013/078164 filed on Oct. 17, 2013 and claims benefit of Japanese Application No. 2012-261196 filed in Japan on Nov. 29, 2012, the entire contents of which are incorporated herein by this reference.

BACKGROUND OF THE INVENTION

1. Field of the Invention

The present invention relates to a substrate connection structure in which a second connector mounted on a second substrate is detachably attachable to a first connector mounted on a first substrate.

2. Description of the Related Art

Endoscopes are used in, e.g., medical fields and industrial fields. Examples of the endoscopes include what are called electronic endoscopes with an image pickup apparatus incorporated in a distal end portion of an insertion portion thereof. For the electronic endoscopes, there is a demand for image quality enhancement, and thus, e.g., an increase in number of pixels in image pickup devices is being pursued.

In the endoscopes, there is a long transmission passage connecting the image pickup apparatus incorporated in the distal end portion of the insertion portion and, for example, a video processor, which is an external apparatus. Therefore, a relay substrate that amplifies a drive signal for an image pickup device is provided inside the endoscope operation portion to enhance the image quality and reduce a diameter of a signal cable inserted inside the insertion portion.

Inside the endoscope operation portion, many incorporated endoscope components are inserted in addition to the signal cable. Examples of the incorporated endoscope components include, e.g., a light guide fiber bundle for supplying illuminating light, an air feeding tube included in an air feeding conduit, a water feeding tube included in a water feeding conduit, a dual-purpose tube that serves as a suction conduit and a treatment instrument conduit, and bending wires that make a bending portion perform a bending operation.

Thus, the relay substrate is configured to have a small size and is provided in the endoscope operation portion in consideration of assembly and repair workability.

For example, Japanese Patent Application Laid-Open Publication No. 2009-277534 indicates a fill-like connector structure that enables reduction in height and space of a connection portion, the connector structure preventing a female connector and a male connector from being separated even when the connector structure is subject to impact or vibration.

SUMMARY OF THE INVENTION

A substrate connection structure according to an aspect of the present invention includes: a first substrate with a first connector mounted on a front face, the first substrate having stiffness; a second substrate with a second connector mounted on a front face facing the front face of the first substrate, the second connector being detachably attached to the first connector, the second substrate having stiffness; and a restricting member including a projection portion, the restricting member including a plate-like member and being detachably attachable to the first substrate by being moved along a planar surface of the first substrate, the projection portion projecting from the front face of the first substrate and regulating a position where the second substrate is disposed relative to the first substrate in a state in which the restricting member is attached to the first substrate, and limiting a direction in which the second substrate is detached when the second connector mounted on the second substrate is detached from the first connector on the first substrate.

DETAILED DESCRIPTION OF THE PREFERRED EMBODIMENT

An embodiment of the present invention will be described below with reference to the drawings.

Figure 1:
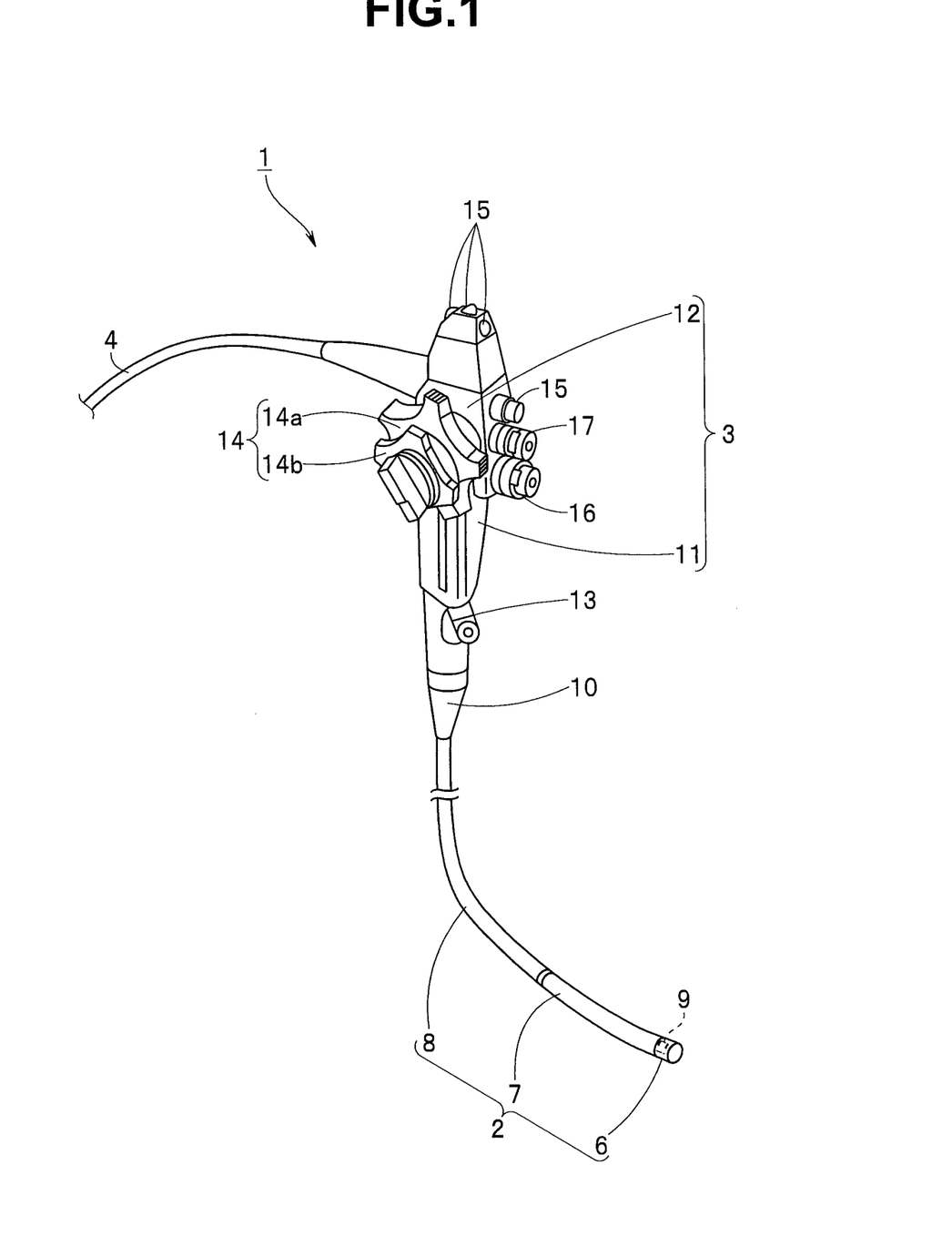
FIG. 1 is a diagram illustrating an endoscope.

As illustrated in FIG. 1, an endoscope 1 includes an insertion portion 2, an operation portion 3 and a universal cable 4. An endoscope connector (not illustrated) is provided at a proximal end portion of the universal cable 4. The endoscope connector is detachably connected to, for example, a camera control unit, which is an external apparatus.

The insertion portion 2 is an elongated member having a long length, which is to be inserted to a site to be observed. The insertion portion 2 includes a distal end portion 6, a bending portion 7 and a flexible tube portion 8, which are continuously provided. The distal end portion 6 incorporates an image pickup apparatus including an illumination optical system that includes a light guide (not illustrated) and an image pickup device 9 including, e.g., a CCD or C-MOS. The bending portion 7 is configured so as to bend in, for example, four directions, upward, downward, rightward and leftward. The flexible tube portion 8 is a tubular member having a long length and flexibility.

The operation portion 3 includes a combination of a first sheathing body 11 and a second sheathing body 12. In the first sheathing body 11, for example, a treatment instrument insertion port 13 is provided. A proximal end portion of the insertion portion 2 is integrally joined and fixed to the distal end side of the first sheathing body 11 via a bend preventing member 10.

At the second sheathing body 12, e.g., a bending operation portion 14, various kinds of switches 15, an air/water feeding button 16 and a suction button 17 are provided. At the bending operation portion 14, for example, bending operation knobs 14a and 14b for performing a bending operation of the bending portion 7 are provided. A surgeon turns, for example, the bending operation knob 14a in a predetermined direction, whereby non-illustrated bending wires are pulled or loosened to bend the bending portion 7 upward.

Note that examples of the various kinds of switches 15 include, e.g., a release switch, a freeze switch and an observation mode selection switch for switching between normal observation and fluorescent observation.

Figure 2:
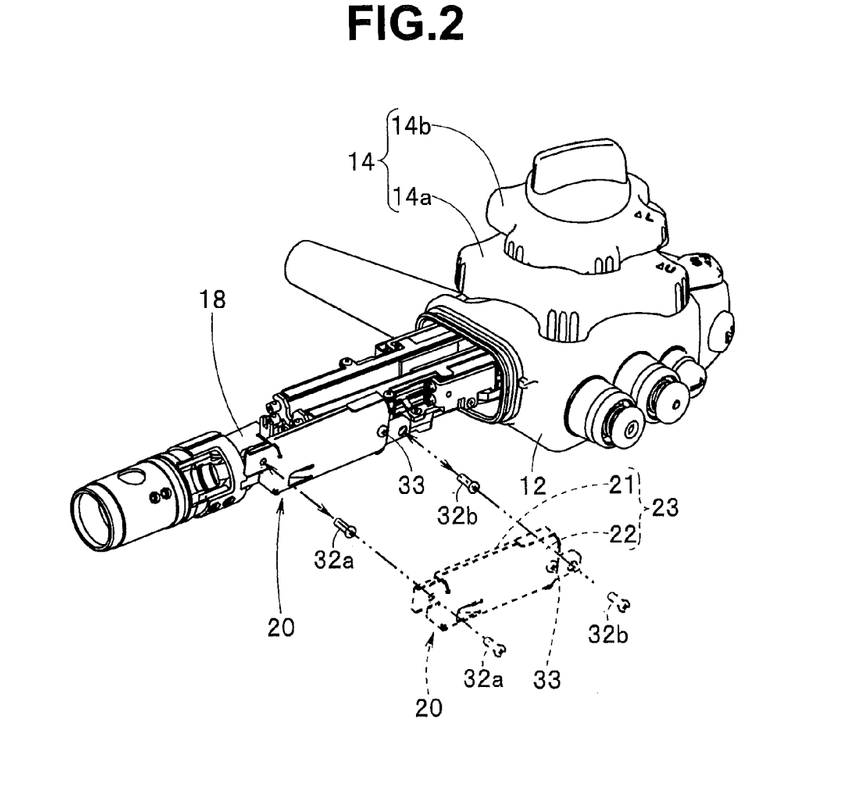
FIG. 2 is a diagram illustrating a relay unit provided inside an operation portion of the endoscope.

As illustrated in FIG. 2, a fixed plate 18, which is an operation portion framework component, is integrally fixed at a predetermined position in the second sheathing body 12 included in the operation portion 3. The fixed plate 18 includes, for example, a stainless steel. The fixed plate 18 is shaped so that various kinds of components provided in the operation portion 3 can be attached to the fixed plate 18 in an optimum manner.

Reference numeral 20 denotes a relay unit. The relay unit 20 includes a housing case 23 including a case body 21 and a cover body 22. The housing case 23 is detachably attached to a predetermined position in the fixed plate 18 via attachment screws 32a and 32b.

Figure 3:
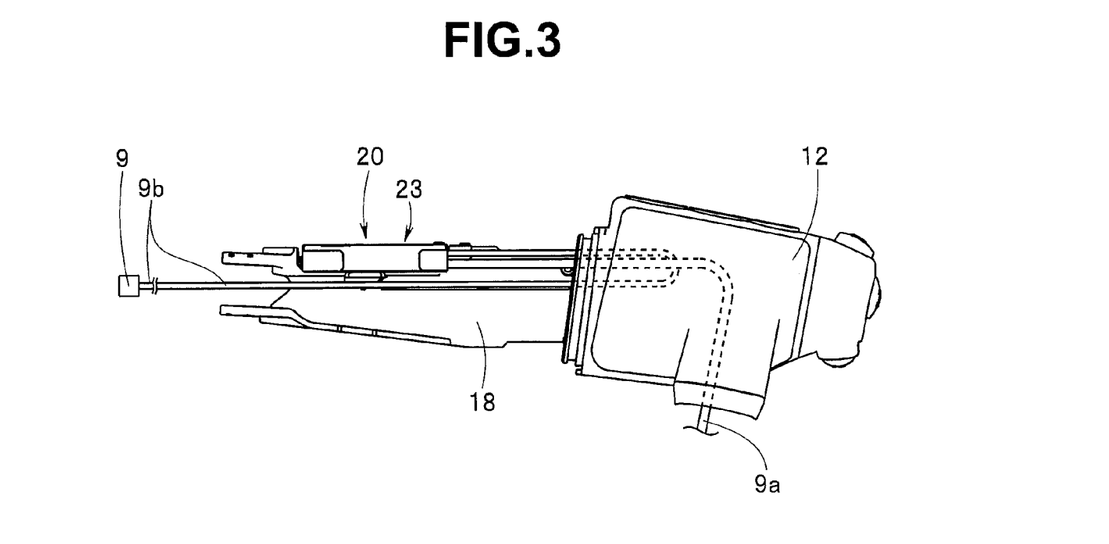
FIG. 3 is a diagram illustrating a relationship between the relay unit, and a first signal cable and a second signal cable.

As illustrated in FIG. 3, a first signal cable 9a and a second signal cable 9b are connected to the relay unit 20.

An end of the first signal cable 9a is connected to, for example, a substrate inside the endoscope connector. The other end of the first signal cable 9a is connected to a first drive signal relay substrate (reference numeral 24 in FIG. 4 and abbreviated as "first substrate"), which will be described later, inside the relay unit 20.

The second signal cable 9b extends from the image pickup device 9 provided in the insertion portion 2. An end of the second signal cable 9b is connected to the image pickup device 9. The other end of the second signal cable 9b is connected to a second drive signal relay substrate (reference numeral 25 in FIG. 4 and abbreviated as "second substrate"), which will be described later, inside the relay unit 20.

In a state in which the relay unit 20 is attached and fixed to the fixed plate 18, the first signal cable 9a and the second signal cable 9b thrust into the housing case 23 from the proximal end face side of the relay unit 20.

Here, e.g., the relay unit 20 and a substrate connection structure provided inside the unit will be described.

Figure 4:
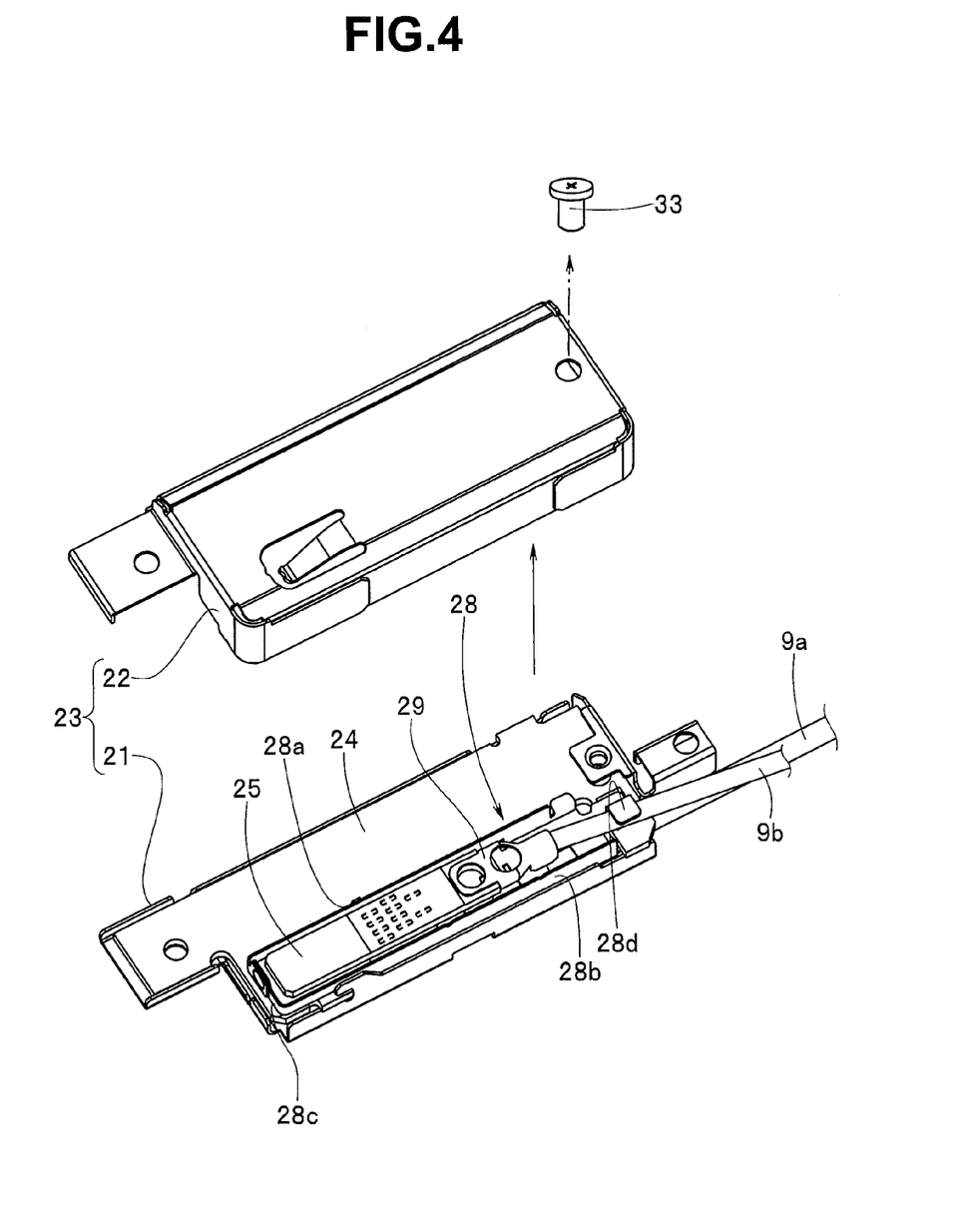
FIG. 4 is a diagram illustrating a configuration of a housing case and, e.g., a first substrate, a second substrate, the first signal cable and the second signal cable arranged in an inner space of a case body.

As illustrated in FIG. 4, the housing case 23 includes the case body 21 and the cover body 22 integrally fixed via a fixing screw 33. The housing case 23 is a shielding case. The case body 21 is configured in a box shape using a shielding member. The cover body 22 is also configured in a box shape using a shielding member. The cover body 22 occludes an opening of the case body 21.

As a result of removing the fixing screw 33 from the housing case 23, the case body 21 and the cover body 22 are separated from each other in such a manner as illustrated in the figure. In an inner space of the case body 21, e.g., the first substrate 24, the second substrate 25, the first signal cable 9a and the second signal cable 9b are arranged.

Figure 5:
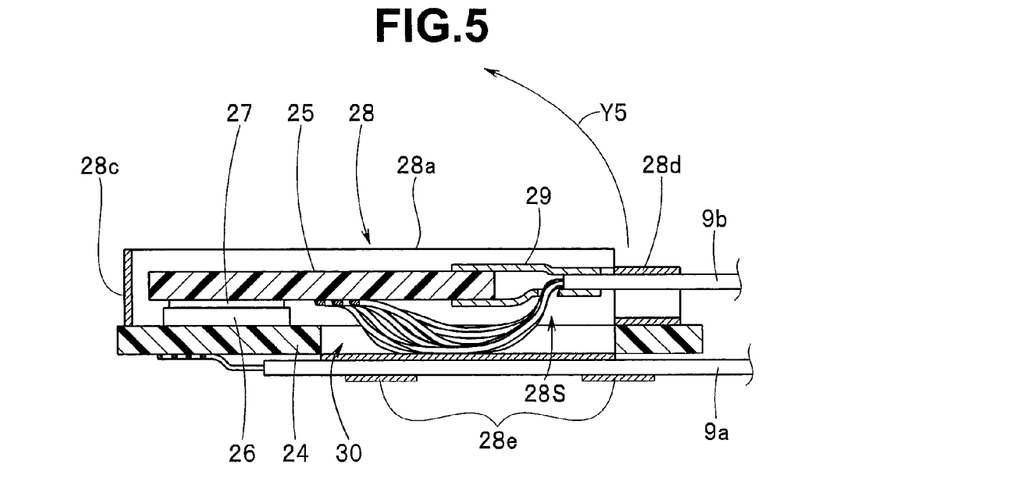
FIG. 5 is a diagram illustrating a state of connection between the first substrate and the second substrate.

As illustrated in FIG. 5, a first connector 26 is mounted on a front face that is one surface of the first substrate 24. A second connector 27 is mounted on a front face of the second substrate 25. The first substrate 24 and the second substrate 25 are integrally joined and electrically connected by connecting the first connector 26 and the second connector 27.

Reference numerals 28a, 28b and 28c illustrated in FIGS. 4 and 5 denote projection portions, which are configured so as to stand from a back face that is another surface of the first substrate 24. Reference numeral 28 indicated in FIG. 5 denotes a restricting member.

The projection portions 28a, 28b and 28c form a regulating portion 28S that regulates a position where the second substrate 25 is disposed on the front face of the first substrate 24. In the present embodiment, the projection portions 28a, 28b and 28c are provided so as to surround predetermined three sides of the second substrate 25.

More specifically, the first projection portion 28a is provided so as to face a long side of the second substrate 25. The second projection portion 28b is provided so as to be opposed to the first projection portion 28a and face the other long side of the second substrate 25. The third projection portion 28c is provided so as to face a short side of the second substrate 25 on which the second connector 27 is mounted.

Figure 6:
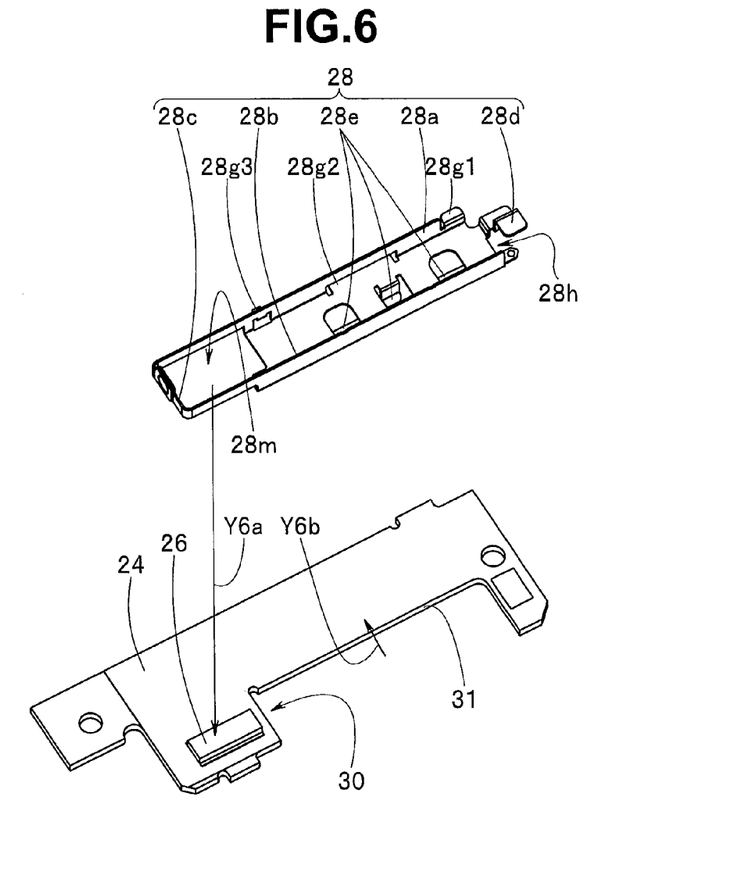
FIG. 6 is a diagram illustrating a configuration of the first substrate and a restricting member disposed in a cutout portion of the first substrate.

Reference numeral 28h in FIG. 6 denotes a short-side open portion. On the short-side open portion 28h in which no projection portions 28a, 28b and 28c are provided in the restricting member 28, the second signal cable 9b extending from the other short side of the second substrate 25 is disposed.

Reference numeral 28d indicated in FIGS. 5 and 6 denotes a second cable holding hook. The second cable holding hook 28d holds an upper face, in the figure, of the second signal cable 9b. As a result of the second cable holding hook 28d holding the upper face of the second cable 9b, the cable 9b is prevented from being swayed in the arrow Y5 direction.

Consequently, the trouble of the second substrate 25 being detached from the first substrate 24 as a result of the cable 9b being swayed in the arrow Y5 direction is prevented.

Reference numeral 28e denotes first cable holding hooks. The first cable holding hooks 28e hold, e.g., a lower face, in the figure, of the first signal cable 9a. As a result of the first cable holding hooks 28e holding, e.g., the lower face of the first cable 9a, the cable 9a disposed along the back face of the first substrate 24 is prevented from being displaced in a longitudinal direction of the first substrate 24.

Note that electronic components are mounted on at least one of the first substrate 24 and the second substrate 25 to amplify a drive signal for the image pickup device 9 in order to overcome signal deterioration such as attenuation and/or dullness.

Reference numeral 29 denotes a cable retainer member. The cable retainer member 29 is a member for positioning and fixing an end portion of the second cable 9b at an end portion of the second substrate 25.

As illustrated in FIG. 6, in the present embodiment, the first substrate 24 and the restricting member 28 are separate members. The restricting member 28 includes the projection portions 28a, 28b and 28c and the cable holding hooks 28d and 28e. In other words, as a result of the restricting member 28 being attached to the first substrate 24, the projection portions 28a, 28b and 28c are provided so as to stand from the front face of the substrate 24.

The restricting member 28 includes a conductive member or a non-conductive member. If the restricting member 28 is intended to provide a shielding effect, the restricting member 28 includes a metal, such as a stainless steel. On the other hand, if the restricting member 28 is intended to prevent electrical connection with peripheral components, the restricting member 28 includes a resin such as polyacetal.

In the restricting member 28, one relief opening (hereinafter abbreviated as "opening") 28m and a plurality of engagement portions 28g are provided in addition to the projection portions 28a, 28b and 28c, the cable holding hooks 28d and 28e and the short-side open portion 28h.

On the other hand, in the first substrate 24, a cutout portion 30 is formed. The cutout portion 30 is configured so that the restricting member 28 is disposed therein.

The engagement portions 28g of the restricting member 28 each include a contact surface. The contact surface of each engagement portion 28g is brought into contact with a front face or a back face of a cutout long side 31 included in the cutout portion 30 of the first substrate 24. More specifically, in the present embodiment, a first engagement portion 28g1 and a third engagement portion 28g3 are brought into contact with and thereby disposed on, for example, the front face of the cutout long side 31. On the other hand, a second engagement portion 28g2 is brought into contact with and thereby disposed on, for example, the back face of the cutout long side 31.

Figure 7:
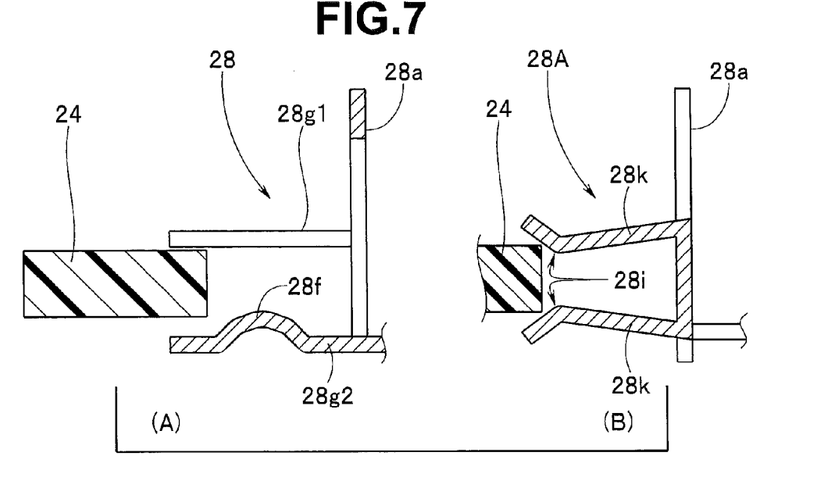
FIG. 7 includes diagrams each illustrating engagement portions of the restricting member.

Then, as illustrated in (A) in FIG. 7, a bulge portion 28f that projects on the contact surface side is provided in the second engagement portion 28g2. The bulge portion 28f is formed at a position that is a predetermined distance from an introduction portion having a width that is larger than a thickness of the first substrate 24. The bulge portion 28f is, for example, a hemispherical bulge portion or a linear bulge portion. The hemispherical bulge portion is formed from the side opposite to the contact face side of the second engagement portion 28g2 by means of, for example, a punch. The linear bulge portion is formed along a longitudinal direction of the second engagement portion 28g2 by means of press work.

Note that a distance in width from a top of the bulge portion 28f to the contact surface of the first engagement portion 28g1 is smaller than the thickness of the first substrate 24. A distance in width from the top of the bulge portion 28f to the contact surface of the third engagement portion 28g3 is smaller than the thickness of the first substrate 24.

With such configuration, the restricting member 28 is disposed so as to be pinched to the cutout long side 31 of the first substrate 24 via the engagement portions 28g1, 28g2 and 28g3 with a predetermined elastic force.

Note that although it has been described above that the bulge portion 28f is provided in the second engagement portion 28g2, the bulge portion 28f may be provided in each of the engagement portions 28g1, 28g2 and 28g3.

Also, as illustrated in (B) in FIG. 7, a restricting member 28A including opposed pinching portions 28k may be configured. The opposed pinching portions 28k form a retainer portion 28i having a width that is smaller than the thickness of the first substrate 24. The retainer portion 28i is formed at a position that is a predetermined distance from an introduction portion having a width that is larger than the thickness of the first substrate 24.

Furthermore, the restricting member 28 may be integrally fixed to the first substrate 24 by means of, e.g., solder, bonding, screws or swaging.

The opening 28m of the restricting member 28 is a through hole that brings the one surface side and the other surface side of the restricting member 28 into communication with each other. In the present embodiment, the opening 28m of the restricting member 28 has a rectangular shape. The opening 28m includes long sides and short sides as with the first connector 26 mounted on the first substrate 24, the first connector 26 including long sides and short sides.

In the present embodiment, dimensions of the long sides and the short sides of the opening 28m are set to predetermined dimensions, which are larger than those of the first connector 26.

Here, a procedure for assembling a relay unit 20 will be described.

A worker prepares, e.g., a first substrate 24, a second substrate 25, a restricting member 28, a case body 21, a cover body 22 and a fixing screw 33. Signal wires in a first cable 9a are connected to connection portions (see reference numeral 24t in FIG. 8B) of the first substrate 24. Signal wires in a second cable 9b are connected to connection portions (not illustrated) of the second substrate 25.

First, the worker disposes the restricting member 28 in a cutout portion 30 of the first substrate 24. Here, as indicated by arrow Y6a in FIG. 6, the worker disposes a first connector 26 in the opening 28m and places the restricting member 28 on a front face of the first substrate 24. Here, engagement portions 28g1, 28g2 and 28g3 are disposed in the cutout portion 30 without being in contact with a cutout long side 31.

Next, the worker disposes the engagement portions 28g1, 28g2 and 28g3 disposed in the cutout portion 30, on the cutout long side 31 in such a manner that the engagement portions 28g1, 28g2 and 28g3 pinch the cutout long side 31. Thus, as indicated by arrow Y6b in FIG. 6, the worker moves the restricting member 28 along a plane of the first substrate 24 to dispose the engagement portions 28g1, 28g2 and 28g3 on the first substrate 24.

Figure 8A:
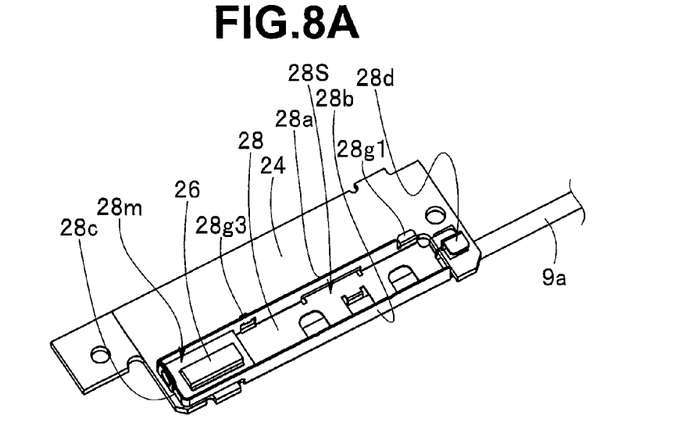
FIG. 8A is a diagram illustrating a front face of the first substrate with the restricting member disposed in the cutout portion.
Figure 8B:
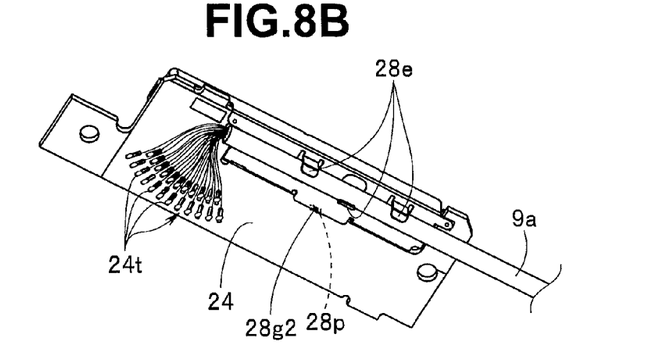
FIG. 8B is a diagram illustrating a back face of the first substrate with the restricting member disposed in the cutout portion.

Then, as illustrated in FIGS. 8A and 8B, the first engagement portion 28g1 and the third engagement portion 28g3 are brought into contact with and thereby disposed on a front face of the cutout long side 31 and a bulge portion 28f of the second engagement portion 28g2 is brought into contact with and thereby disposed on a back face of the cutout long side 31, whereby the restricting member 28 is disposed so as to be pinched to the cutout long side 31 of the first substrate 24. As a result, the restricting member 28 is detachably attached to the first substrate 24 without using an adhesive or screws.

Figure 9:
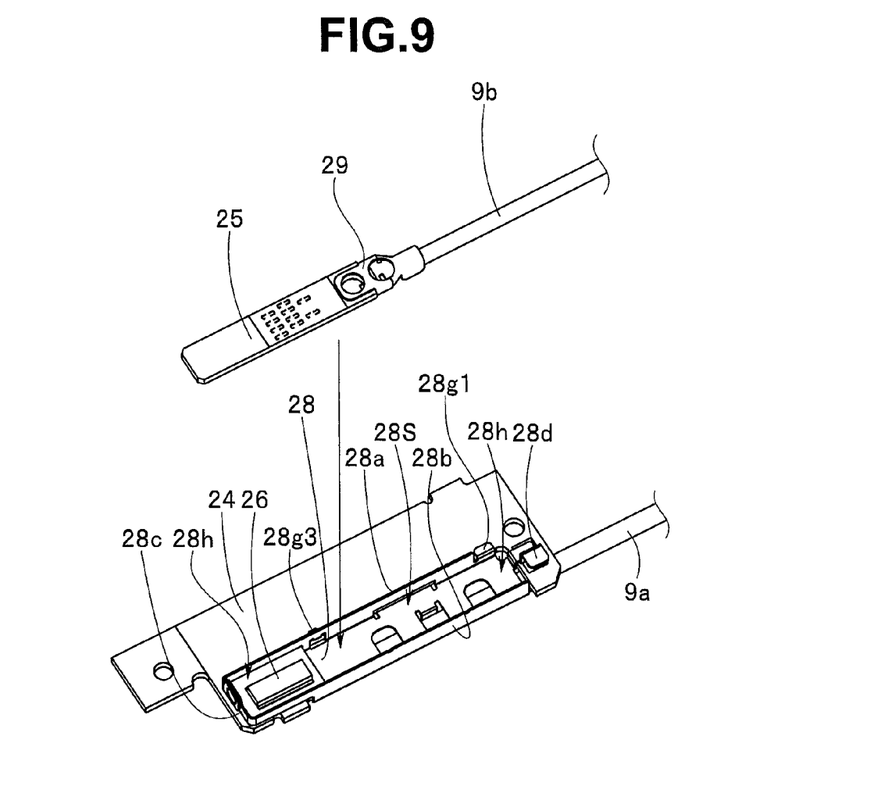
FIG. 9 is a diagram illustrating a relationship between the first substrate with the restricting member disposed in the cutout portion, and the second substrate.

Next, the worker connects a second connector 27 on the second substrate 25 to the first connector 26 on the first substrate 24. Here, as illustrated in FIG. 9, the worker views and checks positions of a regulating portion 28S including three projection portions 28a, 28b and 28c, a short-side open portion 28h and the first connector 26 and determines a direction of the second substrate 25 according to the positions.

Subsequently, the worker disposes the second substrate 25 in the regulating portion 28S. The worker connects the second connector 27 to the first connector 26 and disposes the second signal cable 9b extending from the short-side open portion 28h in the second cable holding hook 28d.

Figure 10:
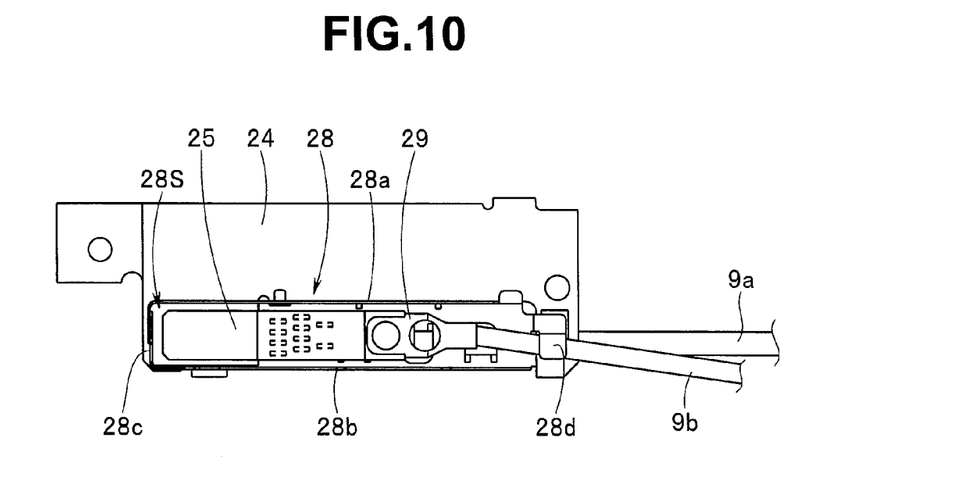
FIG. 10 is a diagram illustrating a state in which the first substrate and the second substrate are connected.

As a result, as illustrated in FIG. 10, connection between the first substrate 24 and the second substrate 25 is completed.

In this connection state, the restricting member 28 disposed on the first substrate 24 so as to be pinched to the substrate 24 is prevented from coming off from the first substrate 24 by the second substrate 25.

Next, the worker disposes the first substrate 24 with the restricting member 28 disposed thereon and the second substrate 25 connected thereto in an inner space of the case body 21.

As a result, as illustrated in FIG. 4 above, e.g., the first substrate 24, the second substrate 25, the first signal cable 9a and the second signal cable 9b are arranged in the inner space of the case body 21.

Next, the worker puts the cover body 22 on the case body 21 to make an opening of the body 21 be occluded by the cover body 22. Then, the cover body 22 and the case body 21 are integrally fixed to each other via a fixing screw 33.

As a result, the relay unit 20 that houses the first substrate 24 and the second substrate 25 in the housing case 23 is configured.

The configuration in which the first substrate 24 and the second substrate 25 are housed in the housing case 23 reliably maintains the connection between the first substrate 24 and the second substrate 25 in the case and prevents the restricting member 28 disposed so as to be pinched from coming off.

Here, detachment of the second substrate 25 from the first substrate 24 will be described with reference to FIG. 10.

When a worker detaches the second substrate 25 from the first substrate 24, the worker views and checks the positions of the regulating portion 28S including three projection portions 28a, 28b and 28c, and the second cable holding hook 28d provided at the first substrate 24 to confirm a direction in which the second substrate 25 is detached.

After the confirmation, the worker takes off the second signal cable 9b disposed in the second cable holding hook 28d. Subsequently, the worker gradually moves the second signal cable 9b in the arrow Y5 direction in FIG. 5 while holding a cable retainer member 29 and an end portion of the second signal cable 9b.

Then, the second substrate 25 is gradually inclined, whereby the second connector 27 and the first connector 26 are gradually disconnected. Then, the second substrate 25 is inclined to a predetermined position, whereby the second connector 27 is detached from the first connector 26, and the second substrate 25 and the first substrate 24 are separated from each other.

As described above, the cutout portion 30 is configured in the vicinity of the first connector 26 mounted on the first substrate 24, and the restricting member 28 including the regulating portion 28S including the projection portions 28a, 28b and 28c, the short-side open portion 28h and the second cable holding hook 28d is provided in the cutout portion 30. As a result, a direction in which the second substrate 25 can be moved when the second substrate 25 is detached from the first substrate 24 is regulated by the projection portions 28a, 28b and 28c.

Accordingly, the worker can easily confirm the direction in which the second substrate 25 is detached by viewing and checking the positions of the regulating portion 28S including the three projection portions 28a, 28b and 28c and the second cable holding hook 28d, which are provided in the first substrate 24. As a result, the trouble of the second substrate 25 being detached in a wrong direction when the worker performs substrate detachment work to detach the second substrate 25 is prevented.

Also, when the worker connects the second substrate 25 to the first substrate 24, the worker can dispose the second substrate 25 to be attached to the first substrate 24, in a correct direction relative to the first substrate 24 by viewing and checking the positions of the regulating portion 28S including the three projection portions 28a, 28b and 28c, the short-side open portion 28h and the first connector 26, which are provided on the first substrate 24.

Accordingly, subsequently, the worker connects the second connector 27 to the first connector 26, and disposes the second signal cable 9b extending from the short-side open portion 28h in the second cable holding hook 28d, enabling easy and reliable connection between the first substrate 24 and the second substrate 25.

Also, as a result of the engagement portions 28g being provided at the restricting member 28, the worker can easily dispose the restricting member 28 on the first substrate 24 without preparing, e.g., solder, an adhesive or screws and without performing, e.g., soldering work, bonding work, thread connection work or swaging work.

Note that if the restricting member 28 includes a conductive member, a ground pattern 28p is provided on a part of a back face of the first substrate 24, the part corresponding to the bulge portion 28f of the second engagement portion 28g2, which is illustrated in FIG. 8B, to electrically connect the ground pattern 28p and the restricting member 28. In addition, shielding wires in the first signal cable 9a are collected in a bundle and connected to the first cable holding hooks 28e.

This configuration enables an increase in shielding effect.

Note that a ground pattern 28p electrically connected to the first engagement portion 28g1 and a ground pattern 28p electrically connected to the third engagement portion 28g3 may be provided on the first substrate 24, respectively.

Note that the present invention is not limited only to the above-described embodiment, and various modifications are possible without departing from the spirit of the invention.

What is claimed is:

1. A substrate connection structure comprising:
a first substrate with a first connector mounted on a front face, the first substrate having stiffness;
a second substrate with a second connector mounted on a front face facing the front face of the first substrate, the second connector being detachably attached to the first connector, the second substrate having stiffness; and
a restricting member including a projection portion, the restricting member including a plate-like member and being detachably attachable to the first substrate by being moved along a planar surface of the first substrate, the projection portion projecting from the front face of the first substrate and regulating a position where the second substrate is disposed relative to the first substrate in a state in which the restricting member is attached to the first substrate, and limiting a direction in which the second substrate is detached when the second connector mounted on the second substrate is detached from the first connector on the first substrate.

2. The substrate connection structure according to claim 1, wherein the projection portion is provided in a vicinity of the first connector on the first substrate and surrounds three sides of the second substrate with the second connector mounted thereon, the second connector being connected to the first connector.

3. The substrate connection structure according to claim 2, wherein a signal cable including a plurality of signal wires collected in a bundle, the signal wires each including an end portion connected to a terminal portion provided on the second substrate, extends from a side of the second substrate, the side being not surrounded by the projection portion.

4. The substrate connection structure according to claim 3, wherein the restricting member includes a cable holding hook that holds the signal cable.

5. The substrate connection structure according to claim 1, wherein the restricting member includes a conductive member.

6. The substrate connection structure according to claim 5, wherein the restricting member is electrically connected to a ground pattern provided on the front face or a back face of the first substrate.

7. The substrate connection structure according to claim 1, wherein the restricting member includes a non-conductive member.

8. The substrate connection structure according to claim 1, wherein the restricting member includes an engagement portion disposed on the first substrate so as to pinch the front face and a back face of the first substrate.

9. The substrate connection structure according to claim 1, wherein the second substrate restricts the restricting member from moving relative to the first substrate in a state in which the second connector on the second substrate is connected to the first connector.

10. The substrate connection structure according to claim 1, comprising a housing case that houses the first substrate, the second substrate and the restricting member, wherein movement of the restricting member relative to the first substrate is restricted in a state in which the first substrate and the restricting member are attached to each other and housed in the housing case.

11. The substrate connection structure according to claim 10, wherein the housing case is provided inside an operation portion of an endoscope.

\* \* \* \* \*